United States Patent [19]
Baud-Grasset et al.

[11] Patent Number: 6,020,184
[45] Date of Patent: Feb. 1, 2000

[54] POLYORGANOSILOXANE BIODEGRADATION METHOD USING A MICROSCOPIC FUNGUS AND SCREENING METHOD

[75] Inventors: Frederic Baud-Grasset; Jean-Claude Palla, both of Lyons, France

[73] Assignee: Rhone-Poulenc Chimie, Cedex, France

[21] Appl. No.: 08/930,126

[22] PCT Filed: May 3, 1996

[86] PCT No.: PCT/FR96/00676

§ 371 Date: Dec. 30, 1997

§ 102(e) Date: Dec. 30, 1997

[87] PCT Pub. No.: WO96/34986

PCT Pub. Date: Nov. 7, 1996

[30] Foreign Application Priority Data

May 5, 1995 [FR] France .................................. 95 05613

[51] Int. Cl.[7] .................................. C12N 1/14; B09B 3/00
[52] U.S. Cl. .................................. 435/254.3; 435/262.5; 435/913; 435/911
[58] Field of Search .................................. 435/254.3, 262, 435/262.5, 911, 913–920

[56] References Cited

U.S. PATENT DOCUMENTS 5,085,998  2/1992  Lebron et al. .......................... 435/262
5,342,779  8/1994  Matsumura et al. ................. 435/262.5

FOREIGN PATENT DOCUMENTS 0 192 237  of 0000  European Pat. Off. ......... A62D 3/00
94/21394   of 0000  WIPO .............................. B09B 3/00
94/21854   of 0000  WIPO .............................. D21C 5/00
94/25190   of 0000  WIPO .............................. B09B 3/00

OTHER PUBLICATIONS

Bilai, V.I., "Certain features of microbiological destruction of organosilicon films on swollen perlite"; Dopov. Akad. Nauk Ukr. RSR, Ser. B, vol. 4, pp. 322–324, 1978.

Chemical Abstracts, vol. 101, No. 17, Oct. 22, 1984, Columbus, Ohio, Abstract No. 147501, Milstein, Oleg et al, "Biodegradation of carbon–14 labeled synthetic lignin polymer by Aspergillus species".

*Primary Examiner*—David A. Redding
*Attorney, Agent, or Firm*—Burns, Doane, Swecker & Mathis, L.L.P.

[57] ABSTRACT

A biodegradation method for polyorganosiloxanes (POS), particularly polydimethylsiloxanes (PDMS), includes contacting the POS with one or more microscopic fungi, preferably in the presence of at least one co-substrate, said fungus being selected from the family of Corticiacea, preferably of the genus Phanaerochaete or Aspergillus, more preferably *Aspergillus sydowii* BJS94, *Phanerochaete sordida* and *Phanerochaete chrysosporium*. A screening method comprises contacting a microscopic fungus with POS, preferably with PDMS, in the presence of a co-substrate, and evaluating the capacity of the fungus to degrade the POS. The fungi disclosed in the invention can be used in the biodegradation method. An isolate of *Aspergillus sydowii* BJS94 is also disclosed.

22 Claims, 1 Drawing Sheet

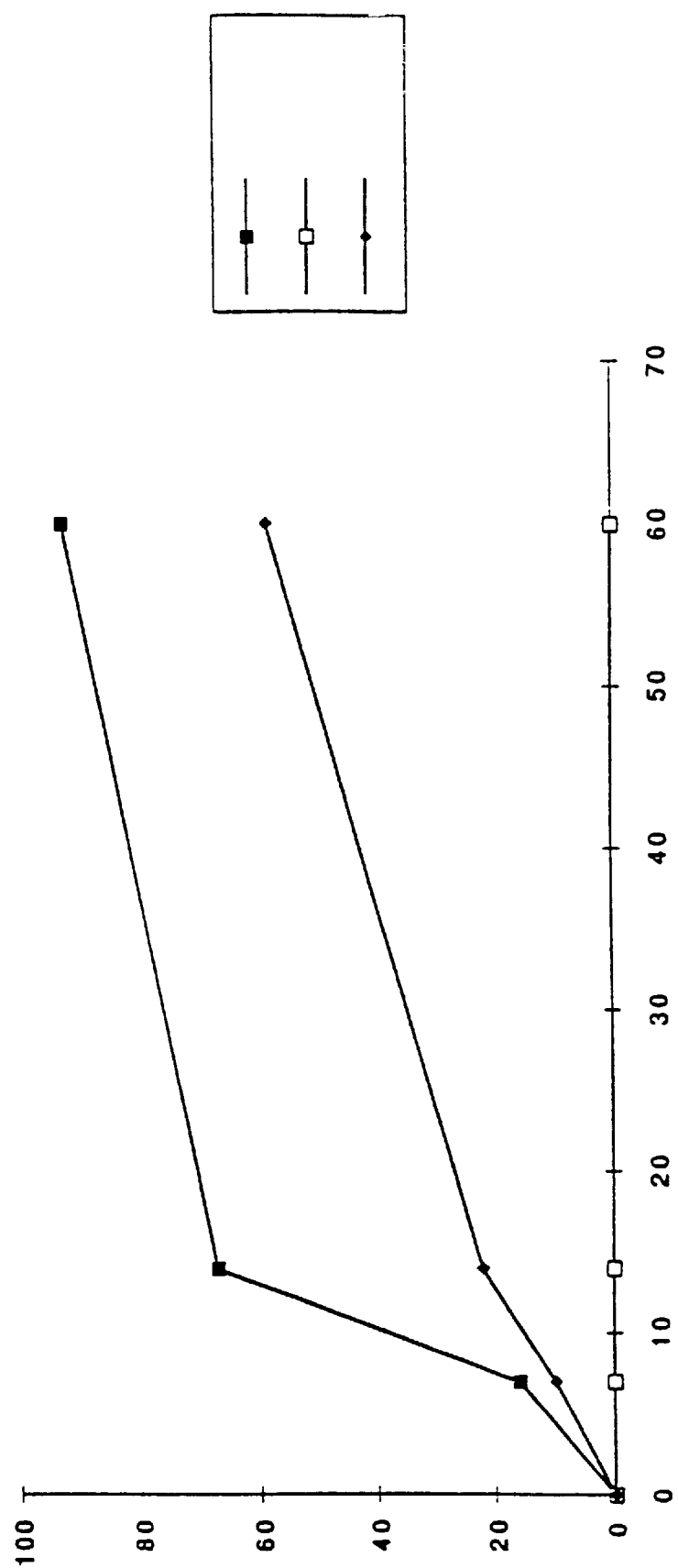

POLYORGANOSILOXANE BIODEGRADATION METHOD USING A MICROSCOPIC FUNGUS AND SCREENING METHOD

The present invention relates to a process for the biodegradation of polyorganosiloxanes (POS) and in particular of polydimethylsiloxanes (PDMS). It also relates to a screening method which makes it possible to select microscopic fungi of use in the context of the biodegradation process.

Until now, silicones were generally regarded as being non-biodegradable.

This state of affairs is today an obstacle to the use of silicones.

Contrary to all expectations, the Inventors have found that, under specific conditions, it is possible to degrade PDMSs with the help of certain microscopic fungi belonging in particular to the genera Phanaerochete and Aspergillus and that this teaching can be extended to POSs in general.

Mention may more particularly be made of *P. sordida* and *P. chrysosporium*, as well as of a recently isolated Aspergillus strain, known as *Aspergillus sydowii* BJS 94, deposited on Feb. 22, 1996 at the CNCM (Collection Nationale de Culture de Microorganismes [National Collection of Microorganism Cultures] of the Pasteur Institute, 28 Rue de Dootour Roux, F-78724 Paris Cedex 15, France) under the reference I 1679. *Aspergillus sydowii* BJS 94 is a filamentous fungus which can degrade glucose and was cultured on malt agar (with 50 g/l malt and 20 g/l agar) from spores. This deposit was made under the Budapest Treaty and all restrictions imposed by the depositor on the availability to the public of the deposited biological material will be irrevocably removed upon the granting of a patent The subject of the present invention is thus a process for the biodegradation of POSs, in particular of PDMSs, wherein the POSs are brought into contact with at least one microscopic fungus, preferably in the presence of at least one cosubstrate, the microscopic fungus being selected in particular from the family of the Corticiacea, preferably from the genus Phanaerochaete, or from the genus Aspergillus, the preferred fungi being selected from the group composed of *P. sordida, P. chrysosporium* and *A. sydowii* BJS 94.

These fungi are freely available from the collections indicated above and in the examples.

The cosubstrate is preferably a source of carbon and of energy which is readily assimilable by the fungus. It is in particular a carbohydrate or a mixture of carbohydrates and very particularly sugar, preferably glucose or sucrose.

According to a first embodiment, preferred in the case of the members of the Phanaerochete genus, of the process according to the invention, the process can be carried out in a medium deficient in nitrogen and preferably, in this case, at an acidic pH, preferably between pH 4.5 and pH 6.

According to a second embodiment of the invention, the process can be carried out in a medium which is not deficient in nitrogen and preferably, then, at a pH in the region of neutrality.

pH in the region of neutrality is understood to mean in particular a pH of between 6.5 and 7.5, preferably of between 6.7 and 7.3 and more preferably of the order of 7.

The process according to the invention can be carried out in a stationary culture but it is preferable, however, to carry it out in an agitated culture with PDMS concentrations preferably ranging up to 5000 mg/l, in particular from 100 to 5000 mg/l, preferably from 250 to 500 mg/l.

Inoculation can be carried out using spores, mycelium or a mixture of both.

Another subject of the present invention, which has for the first time proved that POSs can be degraded by a microscopic fungus, is a screening method which makes it possible to select other microscopic fungi capable of degrading POSs, in particular PDMSs, under the conditions of the invention.

This screening method consists in bringing POS, preferably PDMS, into contact with a candidate microscopic fungus, preferably in the presence of a cosubstrate as defined above.

The screening method can comprise, in addition, a preliminary test which makes it possible to preselect candidates. This preliminary test consists in evaluating the ability of the candidates to grow on POS, preferably PDMS, as sole carbon source. In this case, the candidates responding positively to the preliminary test are then tried out in the screening method proper.

The candidates responding positively to the screening method can be used in the biodegradation process defined above.

The biodegradation process defined above can thus also be employed with the help of the fungi disclosed by the screening method, that is to say responding positively to this method.

The fungi according to the invention can in particular also be used for effluent treatment, in particular in the silicone industry, or in enzymatic catalysis for the purposes of modifying chemical structures or of synthesizing derivatives or novel products of use in the food or pharmaceutical fields and the like. For the purposes of enzymatic catalysis, the parameters of the degradation (amount of fungus, temperature, culture medium, pH, agitation, and the like) can be controlled.

The invention will now be described in more detail with the help of non-limiting implementational examples of the process according to the invention and of the single FIGURE.

BRIEF DESCRIPTION OF THE DRAWINGS

The FIGURE represents the degradation of PDMS 100 cs by two different strains, in comparison with a control, with the time in days on the abscissa and the degree of biodegradation of the PDMS 100 cs in % on the ordinate.

EXAMPLE 1

Screening of Candidates

A series of microscopic fungi are tested (preliminary test) with respect to their ability to grow in liquid medium in the presence of PDMS as sole carbon source. Mycelial growth is evaluated after two weeks. Growth may be observed either at the interface between the aqueous phrase and the PDMS or in the PDMS.

The fungi selected then form the subject of the screening method according to the invention. The following description of examples of the implementation of the biodegradation process is also an illustration of the screening method of the invention.

EXAMPLE 2

This example is carried out in stationary culture:
incubation in 100 ml stoppered flasks.
inorganic medium for fungi, 20 ml (modified Czapeck's medium).

glucose as cosubstrate, 10 g/l.

spore solution (absorbtion at 650 nm 0.4).

silicone oil PDMS 100 cs or 1000 cs (Rhodorsil® PDMS 47 V100 and V1000, Rhône-Poulenc): 5 to 10 g/l.

supplying with pure $O_2$.

The tests are analysed by two successive extrations with pentane (see Example 3), followed by gel permeation chromatography, which makes it possible qualitatively (molecular weight) and quantitatively to determine the remaining concentration of PDMS by comparison of the surface area of the chromatograms corresponding to the samples with those of controls.

*Aspergillus sydowii* BJS 94 is easy to culture (can be cultured on 50 g/l malt agar and 20 g/l agar; inoculation by suspended spores; incubation at 22° C.) and copiously sporulates, which makes it possible, during the implementation of the biodegradation process, to inoculate with spores. The results presented in the following table were obtained with this fungus:

| concentration of PDMS | % biodegradation at 60 days | standard deviation % |
|---|---|---|
| 10 g/l 100cs | 17 | 10 |
| 5 g/l 100cs | 50 | 11 |
| 5 g/l 1000cs | 37 | 15 |

EXAMPLE 3

This example is carried out in agitated culture:

Materials

P. sordida strain: available from FPL (Forest Products Laboratory), U.S. Department of Agriculture, Madison, Wis. 53705, U.S.A., under the reference (KARST.) ERIKSF. and R.y.v.

P. chrysosporium strain: available from DMS, Grisebachstrasse 8, 3400 Göttingen, Germany, under the reference DSM 1547.

polydimethylsiloxane (PDMS): 100 to 1000 cs oil (Rhodorsil®, Rhône Poulenc).

Principle 200 ml of inorganic medium for fungi (medium deficient in nitrogen according to Ming Tien and T. Kent Kirk, edited by Wood Willis A. and Kellogg Scott T., Methods in Enzymology: Biomass, part B, Lignin, Pectin and Chitin, San Diego, Calif., Acad. Press Inc., pages 238–249, vol. 161, 1988), a carbon source comprising 10 g/l glucose, of a solution of P. sordida or P. chrysosporium spores in suspension (absorbtion at 650 mn 0.4), and PDMS (250 or 500 mg/l) are introduced into 500 ml Erlenmeyer flasks.

The flasks are placed on an orbital shaker platform (105 shakes/min), at the rate of three tests per treatment (incubation in medium deficient in nitrogen and pH between 4.5 and 6).

Quantitative Determinations

Quantitative determinations are planned at 0 days, 7 days, 15 days, 30 days and 60 days.

Experimental Technique

Extraction with pentane and then quantitative determination by GPC (gel permeation chromatography).

Extraction Technique addition of 50 ml of pentane.

manual agitation.

agitation for 20 minutes (without biomass) in a separating funnel.

separation by settling.

addition of 50 ml of pentane to the biomass.

ultrasound, 5 min at 140 V.

agitation for 20 minutes in separating funnels.

separation by settling.

recovery of the pentane to be quantitatively determined.

Result

The results of PDMS V100 are combined in FIG. 1, in comparison with a control prepared under the same conditions in the absence of fungus.

Strain RP3=*P. sordida*

Strain RP=*P. chrysosporium*

FIG. 1 clearly shows the high degradation power of RP3 and RP1.

EXAMPLE 4

This example relates to *Aspergillus sydowii* BJS 94, used in agitated culture on PDMS 100 cs. The inorganic medium of Example 2 is taken and incubation is carried out at a pH in the region of neutrality in 500 ml Erlenmeyer flasks, containing 200 ml of the inorganic medium, 10 g/l glucose, spores (absorption at 650 nm=0.4) and 500 mg/l PDMS oil, placed on an orbital shaker platform.

| concentration of PDMS | % biodegradation at 30 days | standard deviation % |
|---|---|---|
| 500 mg/l PDMS 100 cs | 47 | 12 |

We claim:

1. A process for the biodegradation of polyorganosiloxanes (POSs), wherein the POSs are brought into contact with a microscopic fungus, the microscopic fungus being selected from the group consisting of the family of the Corticiacea and the genus Aspergillus.

2. The process according to claim 1, wherein the microscopic fungus is of the genus Phanaerochaete.

3. The process according to claim 1, wherein the fungus is selected from the group composed of *Phanaerochaete sordida*, *Phanaerochaete chrysosporium* and *Aspergillus sydowii* BJS94.

4. The process according to claim 1, wherein the POSs are brought into contact with a microscopic fungus in the presence of a cosubstrate.

5. The process according to claim 4, wherein the cosubstrate is a source of carbon and of energy which is readily assimilable by the fungus.

6. The process according to claim 5, wherein the cosubstrate is a carbohydrate or a mixture of carbohydrates.

7. The process according to claim 6, wherein the cosubstrate is a sugar.

8. The process according to claim 7, wherein the cosubstrate is chosen among the group consisting of glucose and sucrose.

9. The process according to claim 1, which is carried out in a medium deficient in nitrogen.

10. The process according to claim 9, which is carried out at an acidic pH.

11. The process according to claim 10, which is carried out at a pH of between pH 4.5 and pH 6.

12. The process according to claim 1, which is carried out in a medium which is not deficient in nitrogen and at a pH in the region of neutrality.

13. The process according to claim 1, which is carried out in an agitated culture containing POS at a concentration ranging from 100 to 5000 mg/l.

14. The process according to claim 13, wherein the POS is at a concentration ranging from 250 to 500 mg/l.

15. A screening method wherein a microscopic fungus is brought into contact with POS in the presence of a cosubstrate, and the ability of this fungus to degrade the POS is evaluated.

16. Screening method according to claim 15, wherein the cosubstrate is a source of carbon and energy readily assimilable by the microscopic fungi.

17. The screening method according to claim 16, wherein the cosubstrate is a carbohydrate sugar.

18. The screening method according to claim 17, wherein the carbohydrate is a sugar.

19. The screening method according to claim 18, wherein the sugar is chosen among the group consisting of glucose and sucrose.

20. A process for the biodegradation of polyorganosiloxanes (POSs), wherein the POSs are brought into contact with a microscopic fungus, the microscopic fungus being selected from the group consisting of the family of the Corticiacea and the genus Aspergillus, and said fungus responds positively to the method according to claim 15.

21. *Aspergillus sydowii* BJS94 isolate, deposited at the CNCM under the reference I-1679.

22. A method for effluent treatment, wherein the effluent comprises POS, or enzymatic catalysis comprising using the microscopic fungi responding positively to the method according to claim 15.

* * * * *